(12) United States Patent
Styrc et al.

(10) Patent No.: US 8,353,955 B2
(45) Date of Patent: Jan. 15, 2013

(54) PROSTHETIC IMPLANT

(75) Inventors: Witold Styrc, Kopstal (LU); Eric Perouse, Paris (FR)

(73) Assignee: Cormove, Ivry-le-Temple (FR)

( * ) Notice: Subject to any disclaimer, the term of this patent is extended or adjusted under 35 U.S.C. 154(b) by 223 days.

(21) Appl. No.: 12/832,305

(22) Filed: Jul. 8, 2010

(65) Prior Publication Data

US 2011/0034997 A1 Feb. 10, 2011

(30) Foreign Application Priority Data

Jul. 10, 2009 (FR) ........................ 09 54826

(51) Int. Cl.
*A61F 2/24* (2006.01)

(52) U.S. Cl. ...... 623/2.18; 623/2.1; 623/1.26; 623/1.24; 623/2.14

(58) Field of Classification Search .................. 623/1.24, 623/2.1–2.19, 1.26; *A61F 2/24*
See application file for complete search history.

(56) References Cited

U.S. PATENT DOCUMENTS

| 2004/0093070 | A1 | 5/2004 | Hojeibane et al. | |
| 2004/0138135 | A1 | 7/2004 | Nicolette | |
| 2004/0210304 | A1 | 10/2004 | Seguin et al. | |
| 2004/0225353 | A1* | 11/2004 | McGuckin et al. | 623/2.11 |
| 2006/0265056 | A1* | 11/2006 | Nguyen et al. | 623/2.18 |
| 2007/0100435 | A1 | 5/2007 | Case et al. | |
| 2008/0275540 | A1* | 11/2008 | Wen | 623/1.26 |

FOREIGN PATENT DOCUMENTS

EP 1 952 785 A1 8/2008

* cited by examiner

*Primary Examiner* — Thomas J Sweet
*Assistant Examiner* — Jason-Dennis Stewart
(74) *Attorney, Agent, or Firm* — Sughrue Mion, PLLC

(57) ABSTRACT

Prosthetic implant of the type comprising: a tubular support (12) of axis X, which can be deformed between a compressed state with a small diameter and a dilated state with a larger diameter, the tubular support comprising a lattice comprising rhombus-shaped meshes (26), each mesh having a first diagonal (28) parallel to the axis X and a second diagonal (32) perpendicular to the axis X; and at least one resilient membrane (14A, 14B) arranged inside the tubular support. The membrane comprises a fixing portion (48, 52), the fixing portion being fixed to a fixing section (65, 66) delimited by a strand (20A, 20B) of the tubular support, the fixing section being oriented substantially parallel to the axis X.

5 Claims, 8 Drawing Sheets

PROSTHETIC IMPLANT

The present invention relates to a prosthetic implant of the type comprising: a tubular support of axis X, which can be deformed between a compressed state with a small diameter and a dilated rest state with a larger diameter, the tubular support comprising a lattice comprising substantially rhombus-shaped meshes, each mesh having a first diagonal substantially parallel to the axis X and a second diagonal substantially perpendicular to the axis X; and at least one resilient membrane arranged inside the tubular support.

This type of implant is for example a prosthetic valve designed to replace a defective native valve. In a variant, the implant is a tubular endoprosthesis (referred to in English as a stent) designed to reinforce the wall of a blood vessel or to bridge an aneurism.

In prosthetic valves of the above-mentioned type, a portion of a lateral fixing edge of a membrane is fixed to a fixing mesh of the lattice at two opposite vertices along the first diagonal of the mesh.

However, when passing from the compressed state to the dilated rest state, or the other way round, the distance separating the two opposite vertices varies. Because of this, the portion of the lateral edge of the membrane fixed between these two vertices is subject to a variation in tension.

In particular, after manufacturing of the valve and when it is compressed in order to insert it into an implantation catheter, the increase in the distance between the vertices of the mesh causes longitudinal stretching of the portion of the lateral edge of the membrane which therefore has in increased risk of tearing.

This variation in tension may be taken into account when manufacturing the valve. Thus, the portion of the lateral edge of the membrane is initially fixed under excess tension, so that it is fixed at a suitable tension once the support is deployed after implantation of the valve.

However, it is impossible to predict accurately the diameter of the tubular support in the dilated state as this diameter depends on the elasticity of the tissues surrounding the valve, the morphological characteristics of the patient etc. Consequently, the diameter of the tubular support in the dilated state exhibits significant statistical dispersion and the effective tension of the portion of the lateral edge of a membrane also has a large dispersion.

The object of the invention is to propose an improved implant in which the lateral edges are fixed to the tubular support to provide reliable, long-term functioning of said implant.

Accordingly, the invention relates to a prosthetic implant of the above-mentioned type, which is notable in that the membrane comprises a fixing portion, this fixing portion being fixed to a fixing section delimited by a strand of the tubular support, said fixing section being oriented substantially parallel to the axis X.

According to particular embodiments, the prosthetic implant comprises one or more of the following features:
the or each membrane forms a plurality of leaves cooperating together to form an obturator, each leaf having a free downstream edge suitable for resting against one or more other free downstream edges of adjacent leaves to prevent the blood flow from circulating from downstream to upstream along the axis, and for separating from this or these other free downstream edges to allow the blood flow to circulate from upstream to downstream along the axis;
said fixing portion is on a lateral edge of the leaf and is contiguous with the free downstream edge of said leaf;
each leaf is substantially the shape of an isosceles triangle and comprises two lateral edges by which the leaf is connected to the tubular support, and each of the lateral edges of a leaf comprises a downstream portion for fixing the leaf to a fixing section of the tubular support, and an upstream portion, complementary to the downstream portion, fixed to the meshes of the support;
each leaf comprises an upstream point delimiting a triangular cut-out of a shape such that for the edges of the cut-out are fixed to the downstream edges of the corresponding mesh;
the tubular support comprises at least one thread intertwined so as to delimit said meshes, and the strand comprising said fixing section is said at least one thread forming the lattice,
the fixing mesh, one of the segments forming the edges of which comprises the fixing section, is a deformed mesh differing from the substantially rhombus shape of the meshes of the lattice, the segment of the deformed mesh having two points of curvature delimiting between them the fixing section;
a first fixing portion of a first leaf and a second fixing portion of a second leaf are arranged edge to edge, said first and second leaves being adjacent, and a deformed mesh comprises, on a first edge thereof, a first fixing section to carry the first fixing portion and, on a second edge thereof, a second fixing section to carry the second fixing portion, said first and second edges being situated on either side of the first diagonal of the deformed mesh;
said first and second edges of a deformed mesh are the downstream edges of said deformed mesh;
for the tubular support comprising at least one thread intertwined so as to delimit said meshes, said strand is an additional thread intertwined between the threads forming the lattice;
said additional thread is shaped to form at least one substantially U-shaped hairpin section, located along the first diagonal of a mesh known as the fixing mesh, the branches the hairpin forming first and second fixing sections, the first fixing section carrying a first fixing portion of a first leaf and the second fixing section carrying a second fixing portion of a second leaf adjacent to the first leaf, said first and second fixing portions being edge to edge;
said additional thread is saw-tooth-shaped so as to have a first segment sloping relative to the axis and a second segment parallel to the axis, each second segment comprising a fixing section of a fixing portion of a leaf; and
each leaf comprises two fixing tabs, each tab extending substantially in the extension of the free downstream edge of the leaf from the fixing portion of one of the lateral edges of the leaf, each tab being folded round a fixing section of the tubular support.

The invention will be better understood on reading the description below, given solely as an example and with reference to the accompanying drawings, in which.

Figure 1:
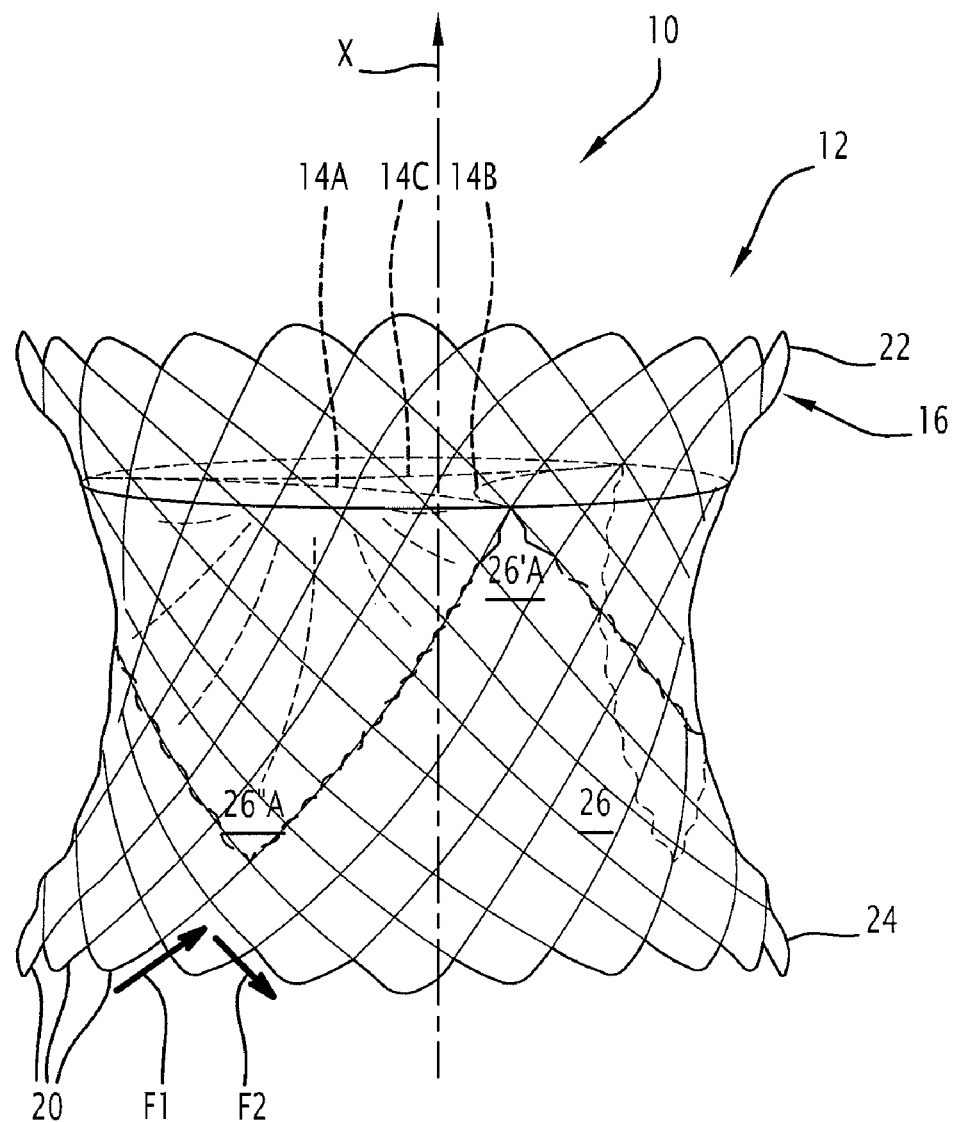
FIG. 1 is a schematic perspective view of a valve according to a first embodiment.

A prosthetic valve according to a first embodiment of the implant according to the invention is illustrated in FIGS. 1 to 8. The valve 10 comprises a tubular support 12 of axis X and a plurality of leaves 14 cooperating together to form an obturator. When the valve is implanted to replace a heart valve, the obturator functions to allow the blood to flow in one direction and prevent the blood from flowing in the opposite direction. The axis X is oriented in the direction of flow allowed by the valve 10, from upstream to downstream.

The tubular support 12 comprises a lattice 16. The lattice 16 consists of intertwined, for example braided or woven, threads. In the embodiment in FIG. 1, six threads, 20A to 20F respectively, are intertwined to form the lattice. A thread 20 is preferably made of a metal, for example stainless steel or nitinol, or an elastomer.

Figure 2:
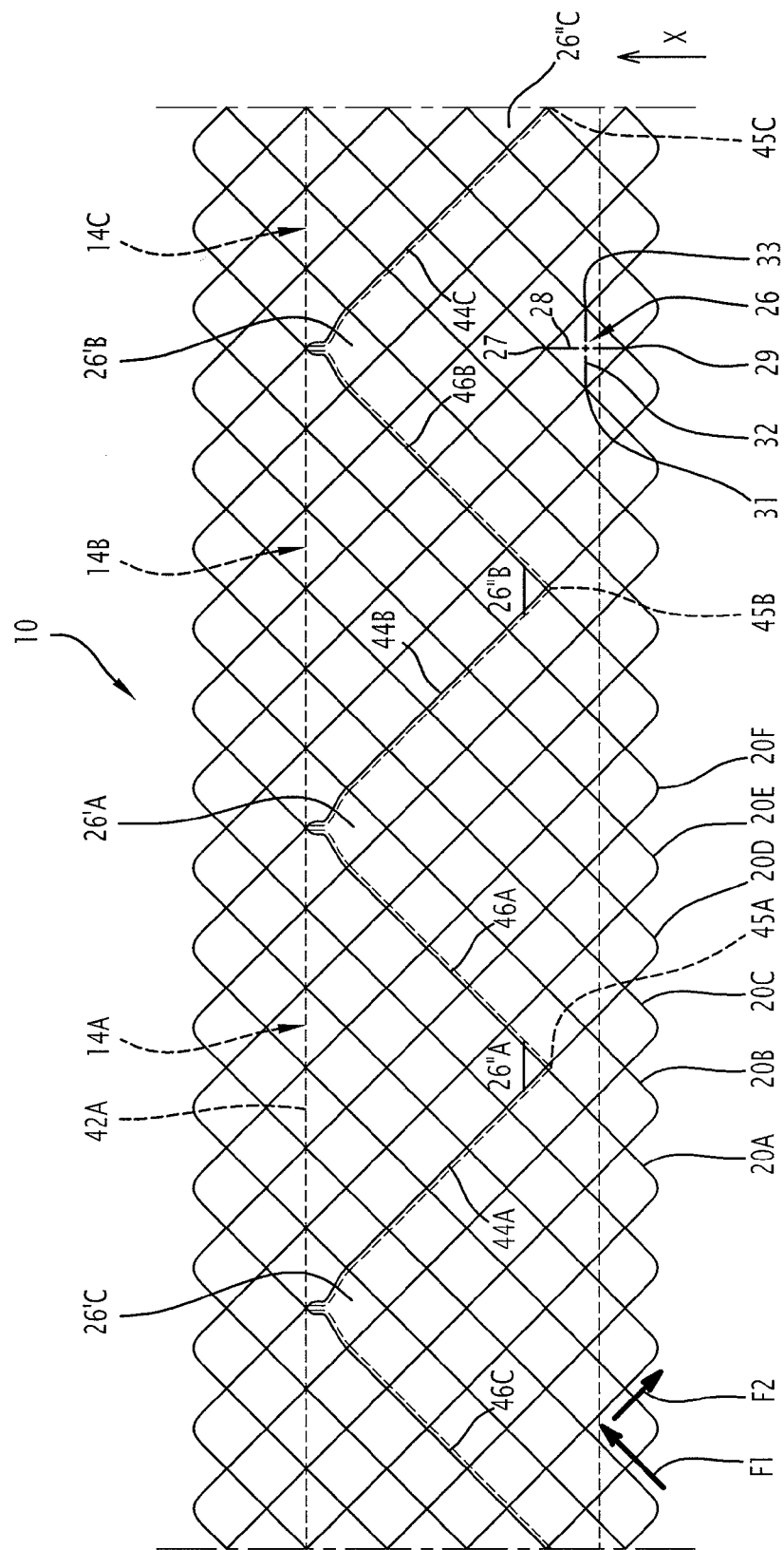
FIG. 2 is a view of the valve of FIG. 1 laid out flat.

A thread, such as the thread 20A, is shaped to describe a helix winding in a first, positive direction about the axis X, as indicated by the arrow F1 in FIG. 1; the thread 20A is then curved in the region of the downstream edge 22 of the support 12. Next the thread 20A is shaped to describe a helix winding in a second, negative direction about the axis X, as indicated by the arrow F2 in FIG. 1. The thread 20A descends as far as the upstream edge 24 of the support 12, where it is curved once more to form a new helix in the first winding direction, then a new helix in the second winding direction etc. As illustrated in FIG. 2, which is a flattened-out view of the valve 10, a thread 20 describes three helixes in the first winding direction and three helixes in the second winding direction before closing on itself.

A thread 20 is inserted along a helix successively over and under the threads that it intersects. Other types of intertwining may be envisaged.

Helixes with the same twisting direction are parallel to one another; in other words, they have an identical pitch. This results in the lattice 16 having substantially rhombus-shaped meshes 26. More specifically, each mesh 26 has a downstream vertex 27, an upstream vertex 29, a left vertex 31 and a right vertex 33. The downstream 27 and upstream 29 vertices are opposite one another along a first diagonal 28 of the mesh 26, arranged substantially parallel to the axis X, whereas the left 31 and right 33 vertices are opposite one another along a second diagonal 32 arranged in a plane substantially perpendicular to the axis X. It will be seen in the figures that the meshes 16 are substantially the shape of a square, which is a particular type of rhombus.

Figure 3:
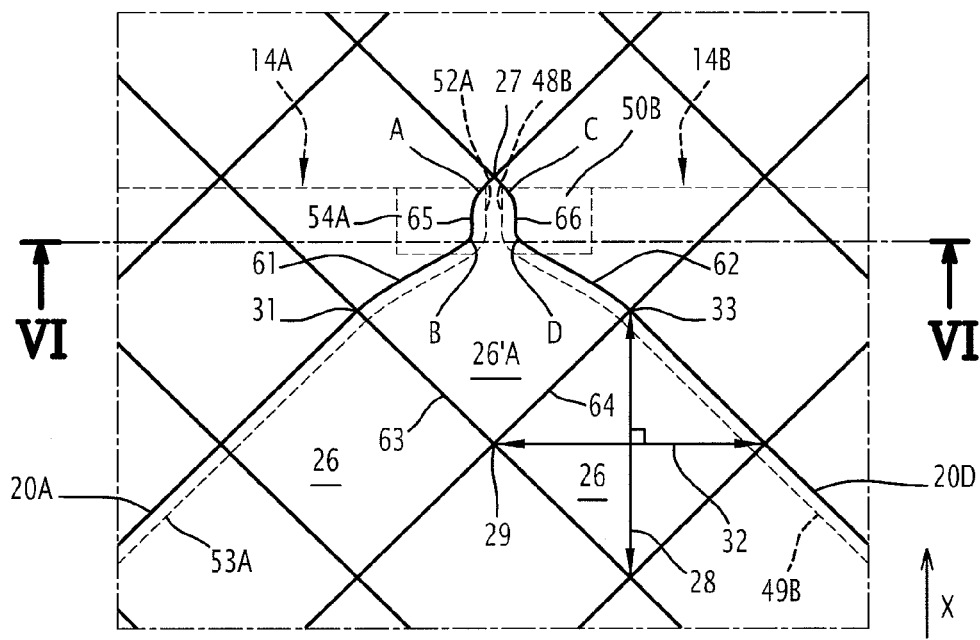
FIG. 3 is an enlarged view of FIG. 2 centred on a deformed mesh for fixing the downstream portion of the lateral edge of a leaf, the tubular support being in the dilated rest state.
Figure 4:
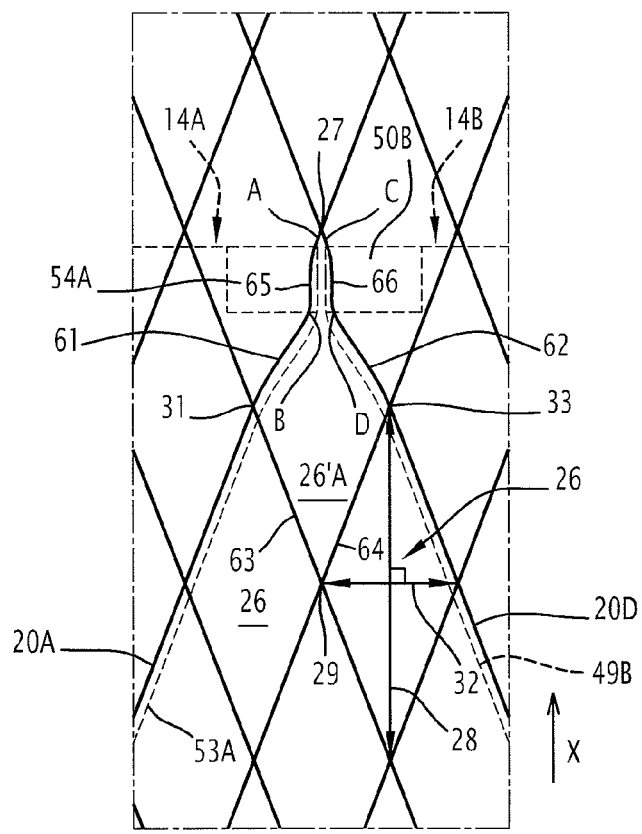
FIG. 4 is a view similar to FIG. 3 with the tubular support in the compressed state.

The lattice 16 has resilient properties and can be deformed spontaneously from a compressed state, in which it has a small diameter, to a dilated state, known as the rest state, in which it has a larger diameter. Because of this resilience, the tubular support 12 rests against the neighbouring tissues and the pressure applied by the support holds the valve 10 in place. When the state changes, a mesh 26 changes shape. FIG. 3 illustrates an enlarged portion of the lattice 16 when the support 12 is in the deployed state, whereas FIG. 4 illustrates the same portion of the lattice 16 when the support 12 is in the compressed state. The length of the edges of a mesh 26 is substantially constant, but the angles at the vertices of the mesh change. Thus, the distance between the upstream 27 and downstream 29 vertices increases whilst the distance between the left 31 and right 33 vertices reduces when the support 12 is compressed, changing from the state illustrated in FIG. 3 to the state illustrated in FIG. 4.

In the embodiment in FIGS. 1 to 8, the obturator of the valve 10 consists of three identical leaves 14, respectively 14A, 14B and 14C, arranged successively and regularly along the circumference of the tubular support 12. Each leaf 14 consists of a membrane made of a polymer film or a layer of organic film, such as pericardium. In a variant embodiment, the valve comprises a single rectangular membrane, rolled up on itself to form a cylinder which is deformed and stitched to the tubular support so as to form the three leaves of the obturator.

Figure 5:
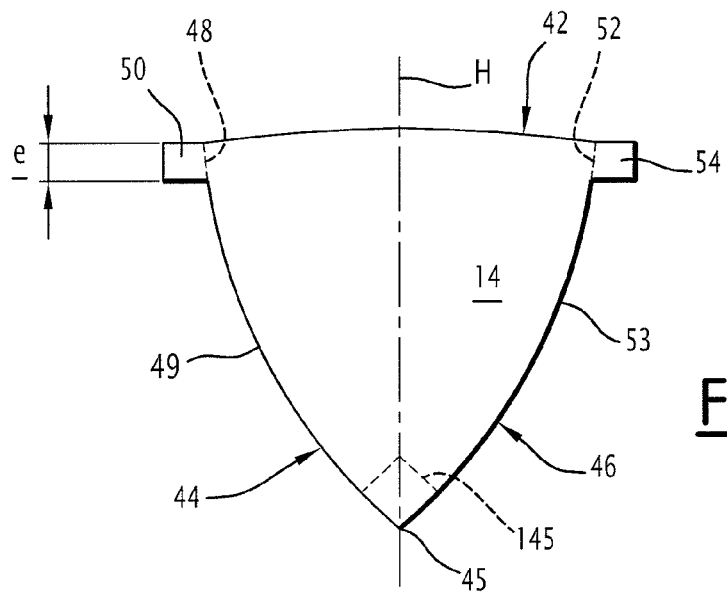
FIG. 5 is a front view of a leaf of the valve of FIG. 1.
Figure 6:
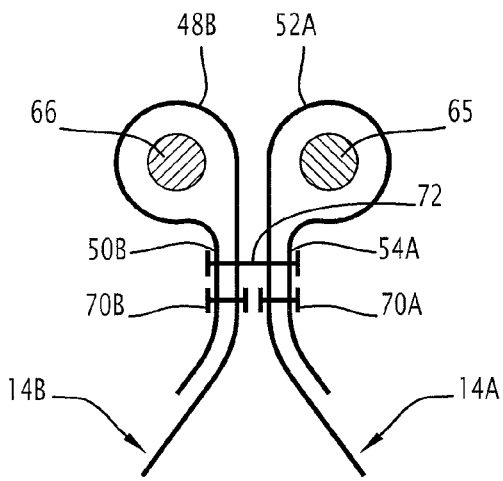
FIG. 6 is a cross-section along the line VI-VI of FIG. 3.

As illustrated in FIG. 5, the shape of a leaf 14 is convergent in the upstream direction, and in particular is shaped substantially as an isosceles triangle. It has a downstream edge 42 forming the base of the triangle, and left and right lateral edges 44 and 46 respectively. The lateral edges extend between one of the ends of the downstream edge 42 and a common intersection point, forming the upstream point 45 of the leaf 14.

Each leaf 14 is arranged inside the tubular support 12 and is connected to the lattice 16 by its two lateral edges 44 and 46. The downstream edge 42 remains free. The free downstream edge of a first leaf is suitable for resting against the two halves of the free downstream edges of the two adjacent leaves to prevent the blood from flowing from downstream to upstream along the axis X, and for separating from these other free downstream edges to allow the blood to flow from upstream to downstream along the axis X.

More precisely, the left edge 44 of the leaf 14 comprises a fixing portion 48 which is contiguous with the free downstream edge 42 and is of height e. The left edge 44 comprises a portion 49 which is complementary to the fixing portion 48, and upstream therefrom. The left edge 44 has a left tab 50 extending from the fixing portion 48, perpendicular to the height H originating from the downstream edge 42, in other words in the extension of the downstream edge 42. The height of the tab 50 is equal to e.

The right edge 46 of the leaf 14 comprises a fixing portion 52, contiguous with the downstream edge 42, having a right tab 54 of height e. The right edge 46 comprises a portion 53 complementary to the fixing portion 52, and upstream therefrom.

A leaf 14 is fixed to the lattice 16 so that each downstream portion 48, 52 is fixed in the region of a deformed mesh 26' of the lattice 16. The lattice 16 comprises as many deformed meshes 26' as leaves 14. Thus, in the embodiment illustrated in the figures, the lattice 16 comprises three deformed meshes, 26'A, 26'B and 26'C respectively.

An enlarged view of the deformed mesh 26'A is shown in FIG. 3. It is delimited by four thread segments 61, 62, 63 and 64. The thread segment 61 passing through the left vertex 31 and the downstream vertex 27 is curved between these two vertices at two points, a downstream point A and an upstream point B respectively. The section of thread between points A and B forms a left fixing section 65. The curvatures conferred on the thread segment 61 in the region of points A and B are such that the thread segment 61 moves away from the helix shape in the first twisting direction, towards the centre of the deformed mesh 26'A and in that the left fixing section 65 coincides substantially with the first diagonal of the deformed mesh 26'A, the left fixing section 65 being as a consequence substantially parallel to the axis X.

Similarly, the thread segment 62 is curved at two points, upstream C and downstream D respectively. The thread segment between points C and D forms a right fixing section 66. The curvatures produced on the thread segment 62 in the region of points C and D are such that the thread segment 62 departs from the helix shape in the second twisting direction, towards the inside of the deformed mesh 26'A and such that the right fixing section 66 coincides with the first diagonal of the deformed mesh 26'A.

The length of the fixing sections 65 and 66 is equal to or slightly greater than the height e of the tabs 50 and 54 of a leaf 14.

The fixing of the leaves 14, for example the leaf 14A and the leaf 14B to the deformed mesh 26'A of the lattice 16 will now be described in detail.

On the right side of the leaf 14A, the right edge 46A thereof is fixed along the thread 20A comprising the segment 61 of the fixing mesh 26'A. More specifically, the downstream right portion 52A is fixed to the left fixing section 65 of the segment 61. The portion 53A complementary to the right edge 46A is fixed along the thread 20A, upstream from point B, the thread 20A thus describing a helix in the first twisting direction.

On the left side of the leaf 14B, the left edge 44B is fixed along the thread 20D comprising the segment 62 of the fixing mesh 26'A. More specifically, the downstream left portion 48B is fixed to the right fixing section 66 of the segment 62. The portion 49B complementary to the lateral edge 44B of the leaf 14B is fixed along the thread 20D, upstream from point D, the thread 20D thus describing a helix in the second twisting direction.

A similar description may be given for fixing the left edge of the leaf 14A and the right edge of the leaf 14C in the region of the deformed mesh 26'C, and for fixing the left edge of the leaf 14C and the right edge of the leaf 14B in the region of the deformed mesh 26'B.

It will be noted that the point 45A of the leaf 14A is fixed to the downstream vertex 29 of the mesh 26"A where the thread 20A coming from the deformed mesh 26'A and carrying the right lateral edge 46A of the leaf 14A intersects the thread 20D coming from the deformed mesh 26'C and carrying the left lateral edge 44A of the leaf 14A.

A fixing portion of a lateral edge of a leaf is fixed to the fixing section of a deformed mesh in the following manner. In the region of the deformed mesh 26'A, as illustrated in a front view in FIG. 3 and in cross-section in FIG. 6, the right tab 54A of the leaf 14A is inserted between the left 65 and right 66 fixing sections, until the fixing portion 52A coincides with the left fixing section 65. The tab 54A is then folded over and applied to the outer surface of the leaf 14A, which is the surface facing the tubular support 12. The tab 54A is fixed to the leaf 14A by a staple 70A. In a variant, the fixing is carried out using a thread. The fixing section 65 in this case is received between the tab 54A and the fixing portion 52A.

For the adjacent leaf 14B, the left tab 50B of the membrane 14B is inserted between the left 65 and right 66 fixing sections in such a way that the left downstream portion 48B is placed in the region of the right fixing section 66. The tab 50B is then folded in the opposite direction from the tab 54A, so as to surround the fixing section 66. It is applied to the outer surface of the leaf 14B, which is the surface oriented towards the tubular support 12. A fixing staple 70B or a thread holds the tab 50B against the leaf 14B. The fixing section 66 is then received between the tab 50B and the fixing portion 48A.

Advantageously, the two adjacent leaves 14A and 14B are fixed together by an additional staple 72 or a suture point produced by means of a thread.

When the assembly is complete, the fixing portions of two adjacent leaves are edge to edge. These fixing portions are applied to one another and oriented along a generatrix of the tubular support 12, in other words parallel to the axis X.

When the support 12 is deformed to change from the dilated rest state to the compressed state, a fixing section of a deformed mesh substantially retains its length and remains oriented substantially parallel to the axis X, as illustrated in FIGS. 3 and 4. Because they are fixed along this type of fixing section, the fixing portions of the different leaves 14 undergo almost no variation in tension during deformation of the support 12.

Moreover, being made integral with a fixing section by the folding of a tab, the fixing portion of a leaf is not really put under tension along the fixing section. It is the tabs which provide some rigidity to the fixing portion. The fixing section may slide slightly inside the loop formed by the folded tab.

In this way, the problems of variation in tension along the downstream portion of the lateral edge of a leaf during deformation of the support are overcome.

Figure 7:
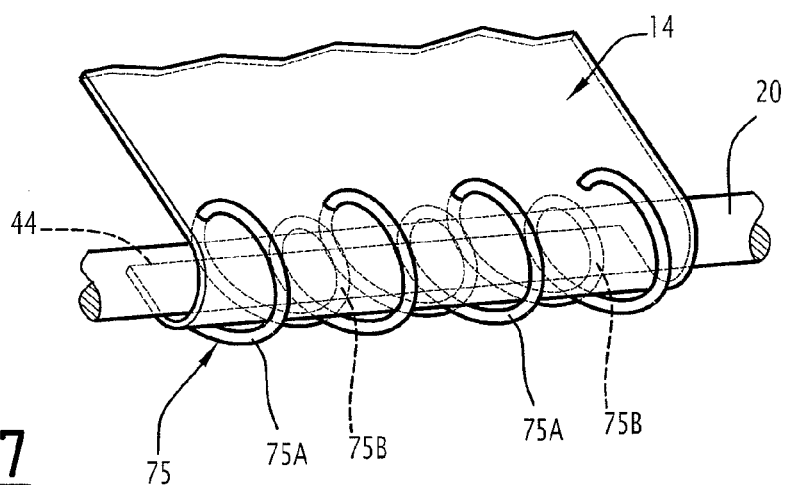
FIG. 7 is a schematic perspective view of the fixing of the lateral edge of a leaf to a thread of the tubular support for the valve in FIG. 1.

FIG. 7 shows in detail an advantageous way of fixing the portion complementary to the lateral edge of a leaf to a thread of the lattice. As illustrated, the edge, for example the left lateral edge 44 of the membrane 14 forms a fold 74 rolled round all or part of the circumference of the thread 20. A suture thread 75 is sewn so as to close the hem formed by the leaf 14 round the thread 20. The suture thread 75 forms loops 75A and 75B round the thread 20. These loops pass alternately above (loop 75A) and below (loop 75B) the leaf 14. A loop 75B of the suture thread 75 situated between the thread 20 and the leaf 14 form a "round turn" to prevent the thread 20 from slipping.

In this way, the complementary portion of a leaf is sewn from the downstream direction, near the fixing portion, to the upstream direction, near the point of the leaf. A method used to fasten off the suture thread 75 is illustrated in detail in FIG. 8. An additional thread 76 is pre-positioned along the complementary portion 53 to be fixed to the lattice so as to form a loop 77 beyond the point 75 of the leaf 14, the two strands 78 and 79 of the additional thread 76 extending downstream beyond the free edge of the leaf. By sewing the thread 75, the loops 75A lock the additional thread 76 between the thread 75 and the leaf 14. At the end of the suture, the end of the thread 75 is passed into the loop 77. The operator withdraws the additional thread 76 by pulling simultaneously on the two strands 78 and 79 of the additional thread 76 along the arrow F3 shown in FIG. 8. The loop 77 draws the end of the thread 75 and causes it to go back between the loops 75A. The additional thread 76 is withdrawn completely and releases the thread 75 which is properly and safely fastened off.

A variant embodiment of a leaf has been illustrated in dashed lines in FIG. 5. According to this variant, a leaf with the general shape of an isosceles triangle comprises a cut-out 145 in the region of the vertex 45 opposite its base 42. The cut-out 145 is such that the area of leaf which has been removed, illustrated by dashes in FIG. 5, is shaped like a mesh 26" of the lattice 16. The leaf modified in this way is fixed to the mesh 26", not on the upstream edges 63 and 64, but on the downstream edges 61 and 62 thereof. The object of this cut-out 145 is to improve the performance of the leaf 14 and the opening of the valve.

Figure 9:
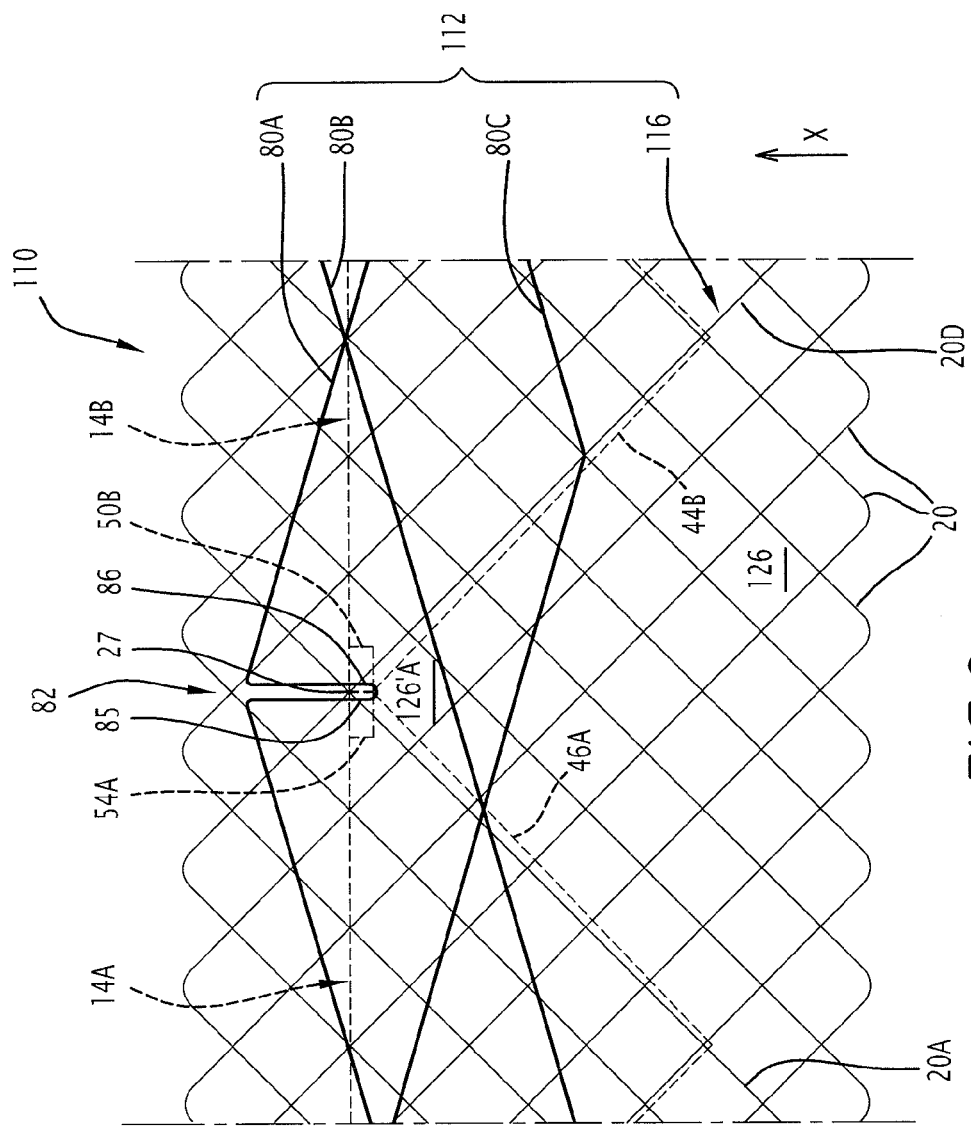
FIG. 9 is a view of a valve laid out flat according to a second embodiment.

A second embodiment of a prosthetic valve has been illustrated in FIG. 9. In this second embodiment, the tubular support 112 of the valve 110 comprises a lattice 116 made up of a plurality of threads 20 and several additional threads 80, intertwined between the threads 20 forming the lattice 116. The additional threads 80 serve as fixing strands for the downstream fixing portion of a lateral edge of a membrane. The lattice 116 has meshes 126 which are all identical. There are no deformed meshes.

Figure 8:
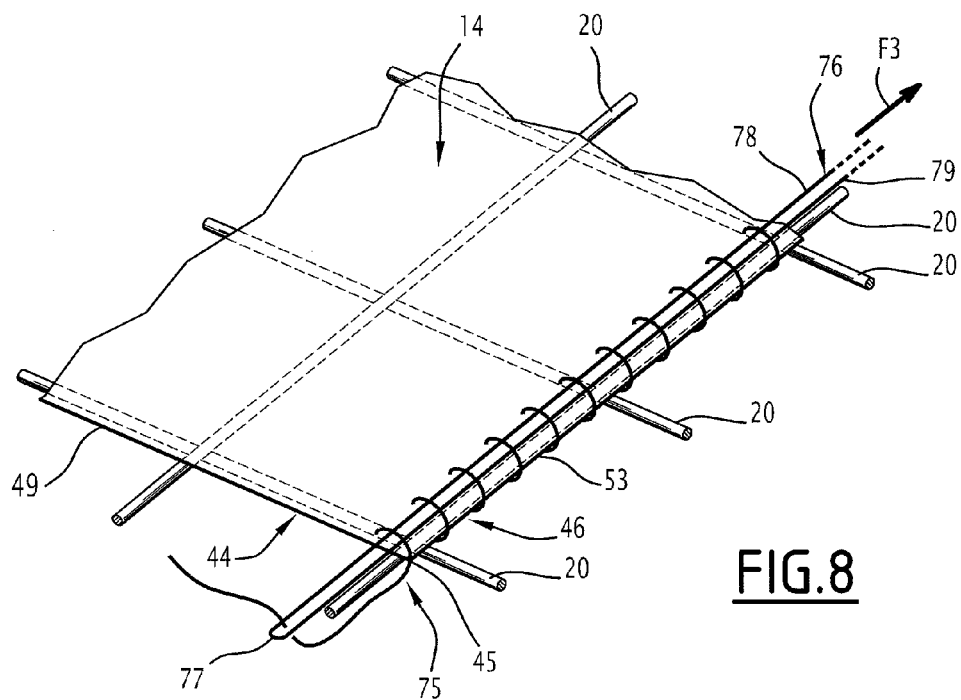
FIG. 8 is a schematic perspective view of the manner in which the thread for fixing a leaf to the lattice is fastened off in the vicinity of the point of the leaf.

An additional thread 80 has characteristics identical to those of a thread 20. In the embodiment of FIG. 8, the tubular support 112 comprises three threads 80A, 80B and 80C.

An additional thread 80, for example the thread 80A, is shaped to form a U-shaped hairpin 82. The hairpin 82 comprises two left and right fixing sections 85 and 86 respectively arranged parallel to the axis X. The hairpin 82 is positioned so that its upstream end, corresponding to the rounded portion of the hairpin, is situated in the region of the downstream vertex 27 of a fixing mesh 126'A.

The right and left downstream portions 52A and 48B respectively of two adjacent leaves 14A and 14B are fixed to each of the fixing sections 85 and 86 respectively of the additional thread 80A. The right and left complementary portions 53A and 49B respectively are fixed upstream from the vertex 27 of the fixing mesh 126'A along the threads 20A and 20D of the lattice passing through said vertex 27.

In the second embodiment, the lateral edge of a leaf is fixed to a fixing section by folding the tab carried by the lateral edge, as described above.

Figure 10:
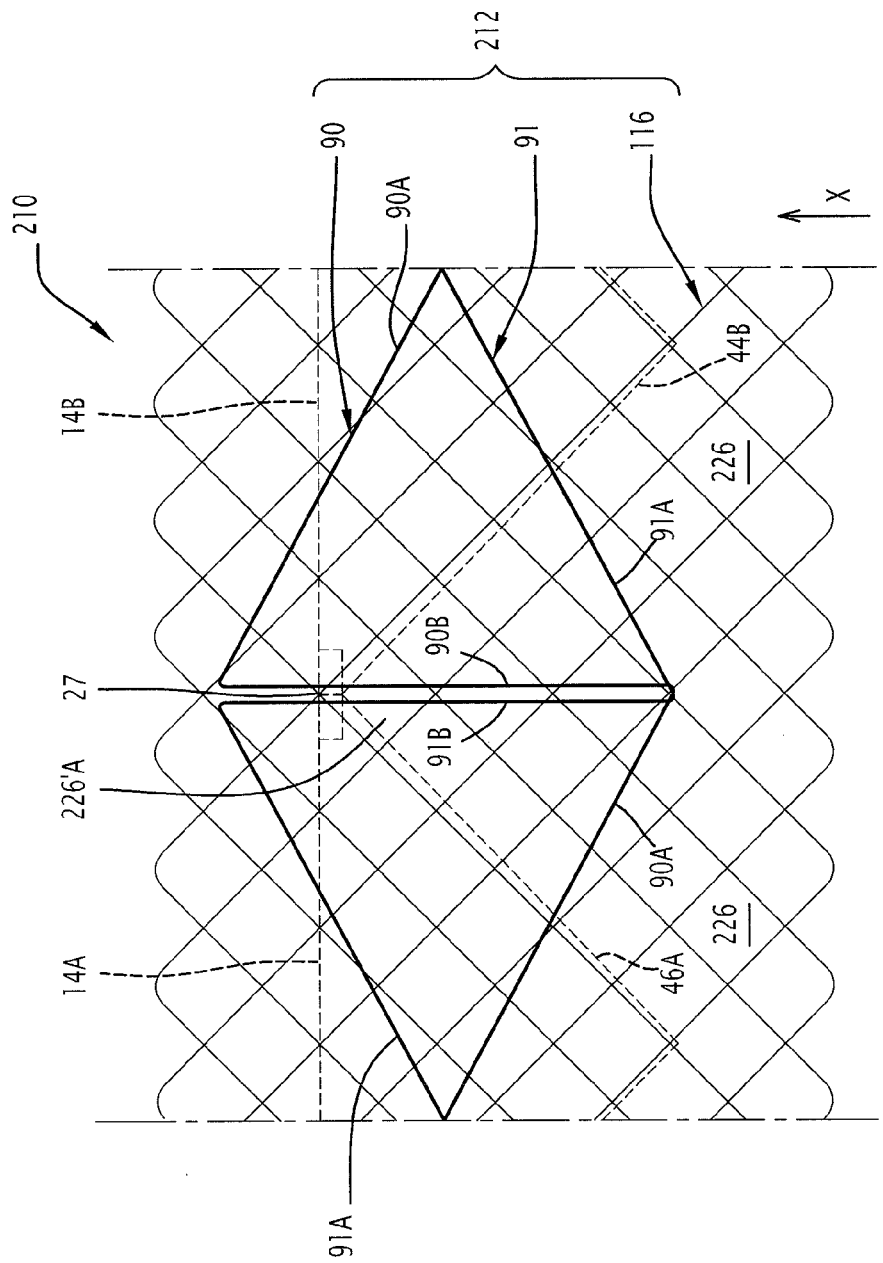
FIG. 10 is an illustration of a valve laid out flat according to a variant of the second embodiment of FIG. 8.

A variant of the second embodiment is illustrated in FIG. 10. The tubular support 212 of the valve 210 comprises a pair of additional threads 90 and 91 serving as fixing strands for the downstream portion of a lateral edge of a leaf. The threads 90 and 91 are shaped so that, flattened out, they have a saw-tooth shape of alternating sloping segments 90A, 91A and longitudinal segments 90B, 91B, arranged along a generatrix of the tubular support 212, in other words substantially parallel to the axis X.

The threads 90 and 91 are mounted on the lattice 216 opposite one another in such a way that a longitudinal segment 90B of the first thread 90 and a longitudinal segment 91B of a second thread 91 coincide with the first diagonal 28 of a fixing mesh 226' of the lattice 216, for example the mesh 226'A.

The fixing portion of the lateral edge of a leaf is fixed to a longitudinal section 90B of an additional thread 90 or 91 in the vicinity of the downstream vertex 27 of the fixing mesh 126'A. The complementary portion of the lateral edge is fixed to a thread 20 of the lattice 116 coming from said vertex 27.

In this second embodiment, the configuration of the additional threads is such that they have a fixing section which is slightly influenced by the deformation of the lattice when the valve is deformed.

Figure 11:
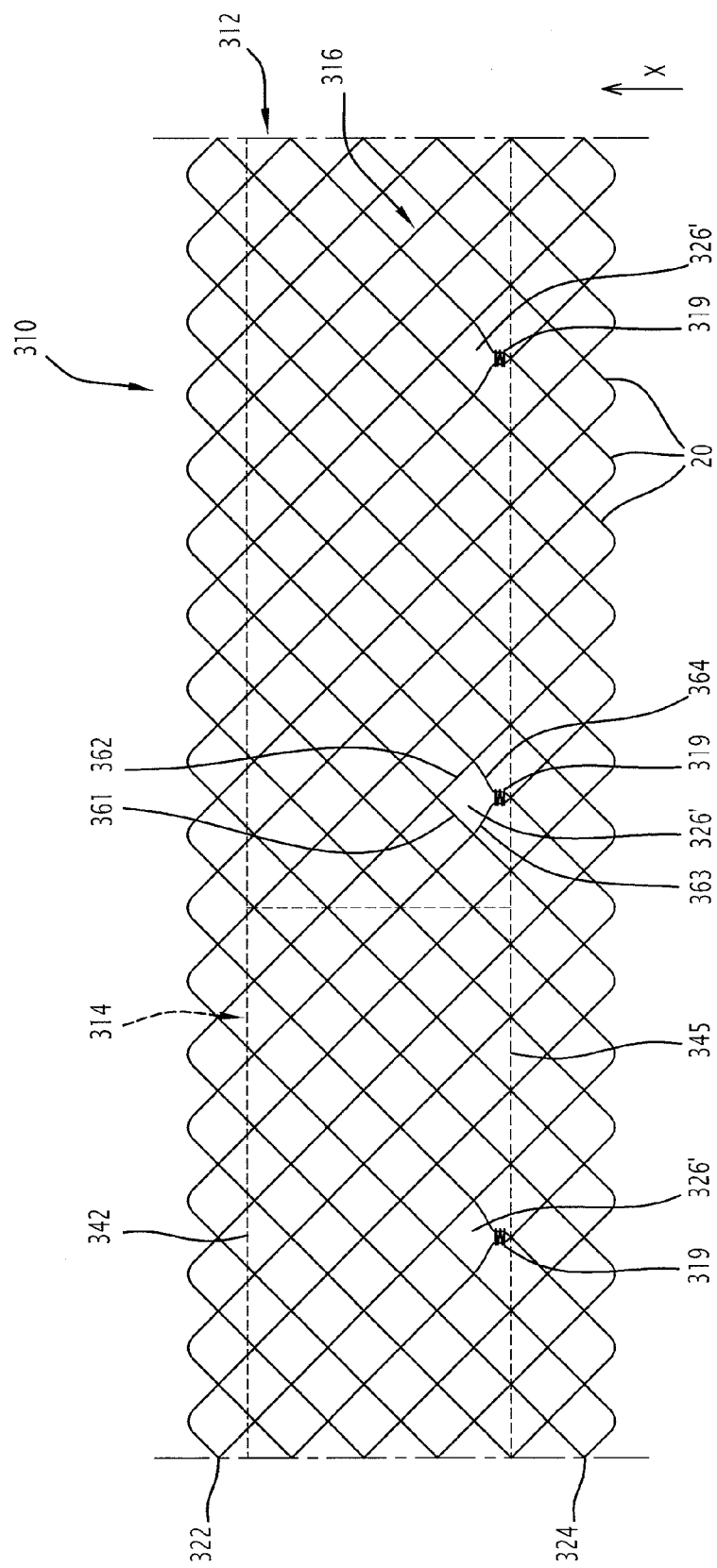
FIG. 11 shows the fixing principle applied to the valve according to the invention for fixing the membrane of an endoprosthesis.

FIG. 11 shows the general principle for fixing a membrane to a deformable tubular support used for the valves of FIGS. 1 to 10 applied to a tubular endoprosthesis 310 used to reinforce the wall of a blood vessel inside which it is implanted or to bridge an aneurism. The endoprosthesis 310 therefore comprises a tubular support 312 of axis X, comprising a lattice 316 of thread 20, and a rectangular membrane 314, folded to form a cylinder of axis X inside the tubular support 312.

The lattice 316 of the tubular support 312 comprises deformed meshes 326',

The downstream edge 42 of the membrane 314 is free. The upstream edge 345 of the membrane 314 is fixed, in the region of fixing portions, to the fixing segments of the lattice 316 by stitches 319.

Figure 12:
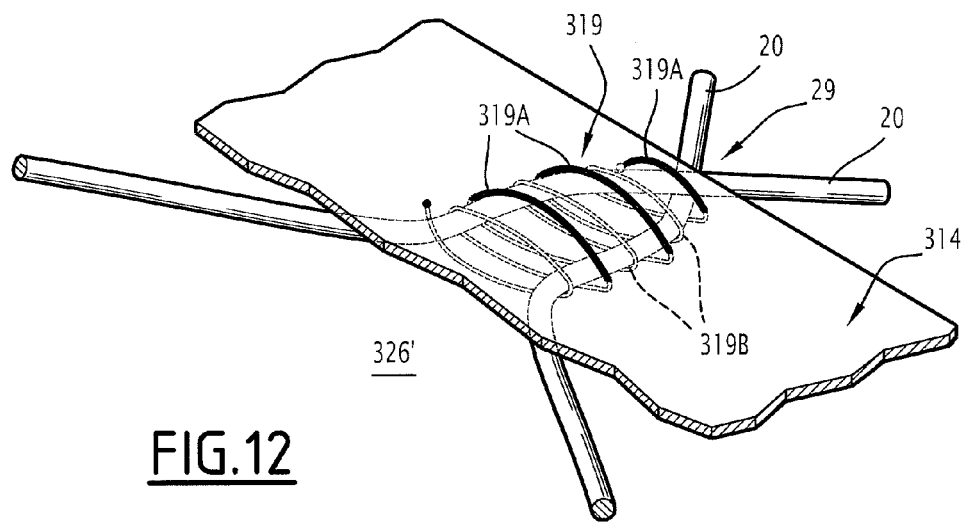
FIG. 12 is an enlarged perspective view of the fixing of the leaf to the tubular support, in the case of the endoprosthesis of FIG. 11.

A stitch 319 of this type has been shown in detail in FIG. 12. It comprises loops 319A passing above the membrane 314 and loops 319B passing between the membrane 314 and the fixing sections of the lattice.

The membrane may be fixed at as many points as necessary. The number of deformed meshes is therefore unlimited.

The invention claimed is:

1. A prosthetic implant of the type comprising:
a tubular support of axis X, which can be deformed between a compressed state with a small diameter and a dilated rest state with a larger diameter, the tubular support comprising a lattice comprising substantially rhombus-shaped meshes, each mesh having a first diagonal substantially parallel to the axis X and a second diagonal substantially perpendicular to the axis X, and
at least one resilient membrane arranged inside the tubular support, comprising a portion which is fixed to fixing section delimited by a strand of the tubular support, said fixing section being oriented substantially parallel to the axis X,
the at least one resilient membrane forming a plurality of leaves cooperating together to form an obturator, each leaf having a free downstream edge suitable for resting against one or more other free downstream edges of adjacent leaves to prevent the blood flow from circulating from downstream to upstream along the axis X, and for separating from the one or more free downstream edges to allow the blood flow to circulate in the upstream to downstream direction along the axis X,
wherein at least one fixing mesh is a deformed mesh of which one of the segments forming its edges comprises the fixing section of the strand, the deformed mesh differing from the substantially rhombus shape of the meshes of the lattice and said segment of the deformed mesh having two points of curvature delimiting between them the fixing section.

2. The prosthetic implant according to claim 1, wherein a first fixing portion of a first leaf and, a second fixing portion of a second leaf are arranged edge to edge, said first and second leaves being adjacent, and in that a deformed mesh comprises, on a first edge thereof, a first fixing section to carry the first fixing portion and, on a second edge thereof, a second fixing section to carry the second fixing portion, said first and second edges being situated on either side of the first diagonal of the deformed mesh.

3. The prosthetic implant according to claim 2, wherein said first and second edges of a deformed mesh are the downstream edges of said deformed mesh.

4. A prosthetic implant of the type comprising:
a tubular support of axis X, which can be deformed between a compressed state with a small diameter and a dilated rest state with a larger diameter, the tubular support comprising a lattice comprising substantially rhombus-shaped meshes, each mesh having a first diagonal substantially parallel to the axis X and a second diagonal substantially perpendicular to the axis X, and
at least one resilient membrane arranged inside the tubular support, comprising a portion which is fixed to fixing section delimited by a strand of the tubular support, said fixing section being oriented substantially parallel to the axis X, the tubular support comprising at least one thread intertwined so as to delimit said meshes, said strand is an additional thread intertwined between the threads forming the lattice, wherein said additional thread is shaped to comprise at least one substantially U-shaped hairpin section, located along the first diagonal of a mesh known as the fixing mesh, the branches of the hairpin forming first and second fixing sections, the first fixing section carrying a first fixing portion of a first leaf and the second fixing section carrying a second fixing portion of a second leaf adjacent to the first leaf, said first and second fixing portions being edge to edge.

5. A prosthetic implant of the type comprising:

a tubular support of axis X, which can be deformed between a compressed state with a small diameter and a dilated rest state with a larger diameter, the tubular support comprising a lattice comprising substantially rhombus-shaped meshes, each mesh having a first diagonal substantially parallel to the axis X and a second diagonal substantially perpendicular to the axis X, and at least one resilient membrane arranged inside the tubular support, comprising a portion which is fixed to fixing section delimited by a strand of the tubular support, said fixing section being oriented substantially parallel to the axis X, the tubular support comprising at least one thread intertwined so as to delimit said meshes, said strand is an additional thread intertwined between the threads forming the lattice, wherein said additional thread is saw-tooth-shaped so as to have a first segment sloping relative to the axis X and a second segment parallel to the axis X, each second segment comprising a fixing section of a fixing portion of a leaf.

\* \* \* \* \*